(12) United States Patent
Phelps et al.

(10) Patent No.: US 9,433,875 B2
(45) Date of Patent: *Sep. 6, 2016

(54) DIVALENT CATION REMOVAL FROM RICH MONOETHYLENE GLYCOL (MEG) FEED STREAMS BY ION EXCHANGE

(75) Inventors: Daniel W. Phelps, League City, TX (US); Luis Eduardo Caires Fernandez, Cypress, TX (US)

(73) Assignee: Cameron International Corporation, Houston, TX (US)

( * ) Notice: Subject to any disclaimer, the term of this patent is extended or adjusted under 35 U.S.C. 154(b) by 938 days.

This patent is subject to a terminal disclaimer.

(21) Appl. No.: 13/593,734

(22) Filed: Aug. 24, 2012

(65) Prior Publication Data

US 2014/0054160 A1 Feb. 27, 2014

(51) Int. Cl.

| B01D 15/36 | (2006.01) |
|---|---|
| C07C 29/76 | (2006.01) |
| C07C 29/80 | (2006.01) |
| C07C 31/20 | (2006.01) |
| B01D 3/14 | (2006.01) |
| B01D 15/00 | (2006.01) |
| C07C 29/74 | (2006.01) |

(52) U.S. Cl.
CPC .............. *B01D 15/00* (2013.01); *B01D 15/36* (2013.01); *B01D 15/362* (2013.01); *C07C 29/76* (2013.01); *B01D 3/143* (2013.01); *C07C 29/74* (2013.01); *C07C 29/80* (2013.01); *C07C 31/202* (2013.01)

(58) Field of Classification Search
CPC .............. B01D 15/00; B01D 15/362; B01D 2259/40083; B01D 2259/40088; B01D 2259/402; B01D 53/04; B01D 3/143; B01J 39/00; B01J 39/04; B01J 49/0008; C07C 29/76; C07C 29/70; C07C 29/84; C07C 29/80; C07C 31/202
USPC .............. 203/14, 38, 41; 210/664, 673, 677; 202/158, 174
See application file for complete search history.

(56) References Cited

U.S. PATENT DOCUMENTS

| 3,574,077 | A | * | 4/1971 | Leo ................................ 210/663 |
|---|---|---|---|---|
| 3,732,320 | A | | 5/1973 | Ford |
| 4,518,396 | A | | 5/1985 | Rawson |
| 5,294,305 | A | * | 3/1994 | Craft et al. ...................... 203/28 |
| 5,817,889 | A | * | 10/1998 | Pondebat et al. .............. 568/679 |
| 5,922,198 | A | | 7/1999 | Kelly et al. |

(Continued)

FOREIGN PATENT DOCUMENTS

| CN | 20101115718 | 7/2010 |
|---|---|---|
| GB | 1219018 | 1/1971 |
| WO | WO9511876 | 5/1995 |

*Primary Examiner* — Renee E Robinson
*Assistant Examiner* — Jonathan Pilcher
(74) *Attorney, Agent, or Firm* — Gable Gotwals

(57) ABSTRACT

A system and process for removing divalent cations from a rich MEG feed stream is presented. An ion exchange bed containing a cation exchange resin adsorbs the divalent cations in the rich MEG feed stream as it flows through the ion exchange bed. After the divalent ions have been removed, the feed stream flows through a flash separator and a distillation column to reclaim MEG. Alternatively, the feed stream flows through a distillation column to regenerate MEG. The spent cation exchange resin may be regenerated in place using a regeneration brine comprised of sodium chloride and water. After use, the regeneration brine may be disposed as waste or recycled to the brine storage tank and re-used to regenerate the cation exchange resin.

6 Claims, 2 Drawing Sheets

(56) References Cited

U.S. PATENT DOCUMENTS

| | | | |
|---|---|---|---|
| 6,023,003 A * | 2/2000 | Dunning | C07C 41/42 568/858 |
| 6,242,655 B1 | 6/2001 | Husain | |
| 6,425,942 B1 | 7/2002 | Forster | |
| 7,232,505 B2 * | 6/2007 | Laborie et al. | 203/18 |
| 8,808,546 B2 * | 8/2014 | Phelps et al. | 210/664 |
| 2010/0191023 A1 * | 7/2010 | Chen | 568/920 |
| 2014/0058140 A1 * | 2/2014 | Phelps et al. | 568/917 |

* cited by examiner

DIVALENT CATION REMOVAL FROM RICH MONOETHYLENE GLYCOL (MEG) FEED STREAMS BY ION EXCHANGE

BACKGROUND

This invention relates to systems and processes designed to treat monoethylene glycol (MEG) used in the oil and gas industry, especially in offshore locations, to control the formation of hydrates. More particularly, the invention relates to MEG reclamation or regeneration processes that are designed to remove divalent cations from a rich MEG feed stream.

In the oil and gas industry, lean (dry) MEG is mixed with the water in a produced stream to control the formation of hydrates within the stream. The now rich (wet) MEG is, in turn, dried by way of a MEG reclamation or MEG regeneration process so that the MEG can be re-used in hydrate control. The lean MEG cannot be recovered by simply distilling the rich MEG and water in conditions of high salt concentration because the rich MEG is loaded with dissolved salt ions from the produced water. Sodium chloride is commonly the most concentrated salt in the produced water, but it may also contain dissolved divalent salts of magnesium, calcium, strontium, and barium. If these divalent cations are not removed or controlled at a low concentration, their high solubility in MEG will alter the physical properties of the MEG, eventually leading to failure of the reclamation or regeneration process.

In the current process for separating divalent cations from the rich MEG feed stream, the ions react with carbonate or hydroxide anions to form insoluble salt crystals, which are then removed from the feed stream. This process generally requires the addition of caustic and acid to completely remove the divalent cations and to neutralize the feed stream before it enters the MEG reclamation or MEG regeneration process.

The time and temperature of the current separation process must be strictly controlled. In addition, the process requires large and expensive equipment, as well as additional chemicals that are not inherently available as part of the MEG reclamation or MEG regeneration process. These chemicals must be obtained from outside sources which can be very expensive, particularly when delivered to offshore platforms in remote parts of the world. The chemicals may also be a safety concern, require specialized handling and storage, and increase training, reporting, and recordkeeping requirements. The current separation process also produces a carbonate salt in the form of a solid or slurry material that is generally insoluble and requires disposal as a waste. Proper disposal of this material can be expensive, time-consuming, and labor-intensive. Disposal is even more difficult in offshore applications where temporary storage space and transportation to an approved disposal site are not readily available.

A need exists for systems and processes for removing divalent cations from rich MEG feed streams in order to improve the efficiency of the MEG reclamation or MEG regeneration process and to prevent the accumulation of salts inside the process equipment. A need also exists for systems and processes that are less expensive, easier to operate, do not require large amounts of space or additional chemicals, and facilitate the disposal of process waste streams.

SUMMARY OF THE INVENTION

A system for removing divalent cations from a rich MEG feed stream is presented. The system includes an ion exchange bed containing a cation exchange resin that adsorbs the divalent cations in the rich MEG feed stream as it flows through the bed. After the divalent cations have been removed, the feed stream flows through a flash separator and a distillation column to reclaim MEG. Alternatively, the feed stream flows through a distillation column to regenerate MEG. The spent cation exchange resin may be regenerated, without removing it from the ion exchange bed, using a regeneration brine. The regeneration brine may be comprised of distilled water that is produced during the MEG reclamation or MEG regeneration process. The regeneration brine may also be comprised of sodium chloride that is produced during the MEG reclamation process. After use, the regeneration brine may be disposed of as waste or recycled to the brine storage tank and re-used to regenerate the cation exchange resin.

A process for removing divalent cations from a rich MEG feed stream is also presented. The process includes the steps of providing an ion exchange bed containing a cation exchange resin and passing the rich MEG feed stream through the bed so that the divalent cations are adsorbed to the resin. The process may also include the step of MEG reclamation or MEG regeneration. A regeneration brine may be used to regenerate the spent cation exchange resin without removing it from the ion exchange bed. The regeneration brine may be comprised of distilled water produced during the MEG reclamation or MEG regeneration process. The regeneration brine may also be comprised of sodium chloride that is produced during the MEG reclamation process. After use, the regeneration brine may be disposed of as waste or recycled to the brine storage tank and re-used to regenerate the cation exchange resin.

The objects of this invention are to (1) provide a more efficient process to remove divalent cations contained in a rich MEG feed stream before the stream enters a MEG reclamation or MEG regeneration process; (2) simplify the removal process by eliminating required conditions for time and temperature; (3) reduce the volume, footprint, and cost of the processing equipment typically required to remove divalent cations from the rich MEG feed stream; (4) provide a renewable or reusable bed for divalent cation removal; (5) provide a process for physical separation of the divalent cations from the rich MEG feed stream, thus eliminating the need for additional chemicals; and (6) facilitate the disposal of waste streams.

ELEMENTS AND NUMBERING USED IN THE DRAWINGS AND THE DETAILED DESCRIPTION

Figure 1:
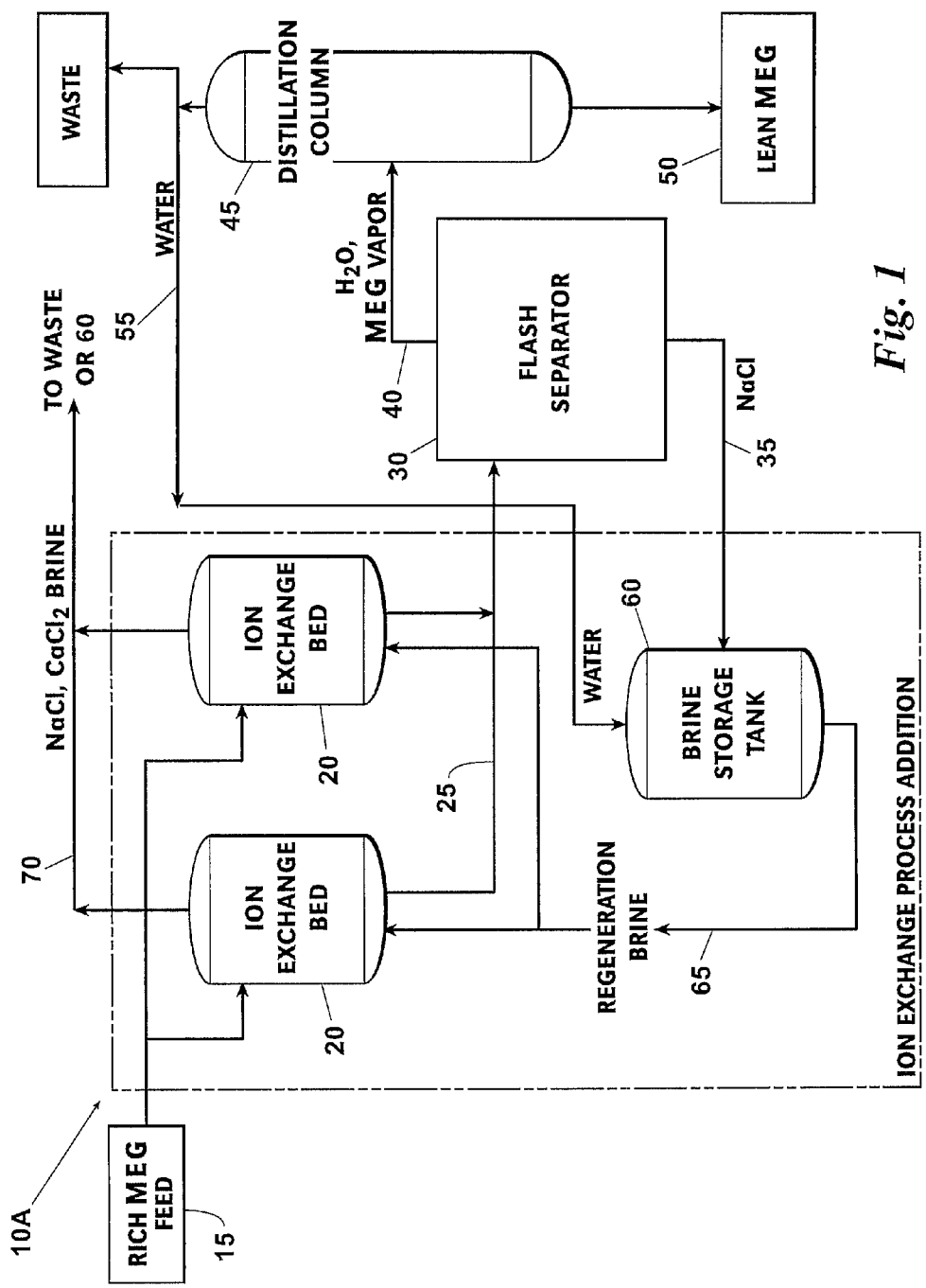
FIG. 1 presents an embodiment of a process for removing divalent cations from a rich MEG feed stream as part of a MEG reclamation process, practiced according to this invention.

10 Divalent cation removal process
15 Rich MEG feed stream
20 Ion exchange bed
25 Rich MEG stream with the majority of divalent cations removed
30 Flash separator 35 Sodium chloride waste stream
40 Vaporized water and MEG stream
45 Distillation column
50 Lean MEG
55 Distilled water
60 Brine storage tank
65 Regeneration brine
70 Waste stream of sodium chloride and calcium chloride brine
80 Sodium chloride
85 Rich MEG feed stream
90 Rich MEG stream with the majority of divalent cations removed
95 Vaporized water

DETAILED DESCRIPTION OF THE PREFERRED EMBODIMENTS

Figure 2:
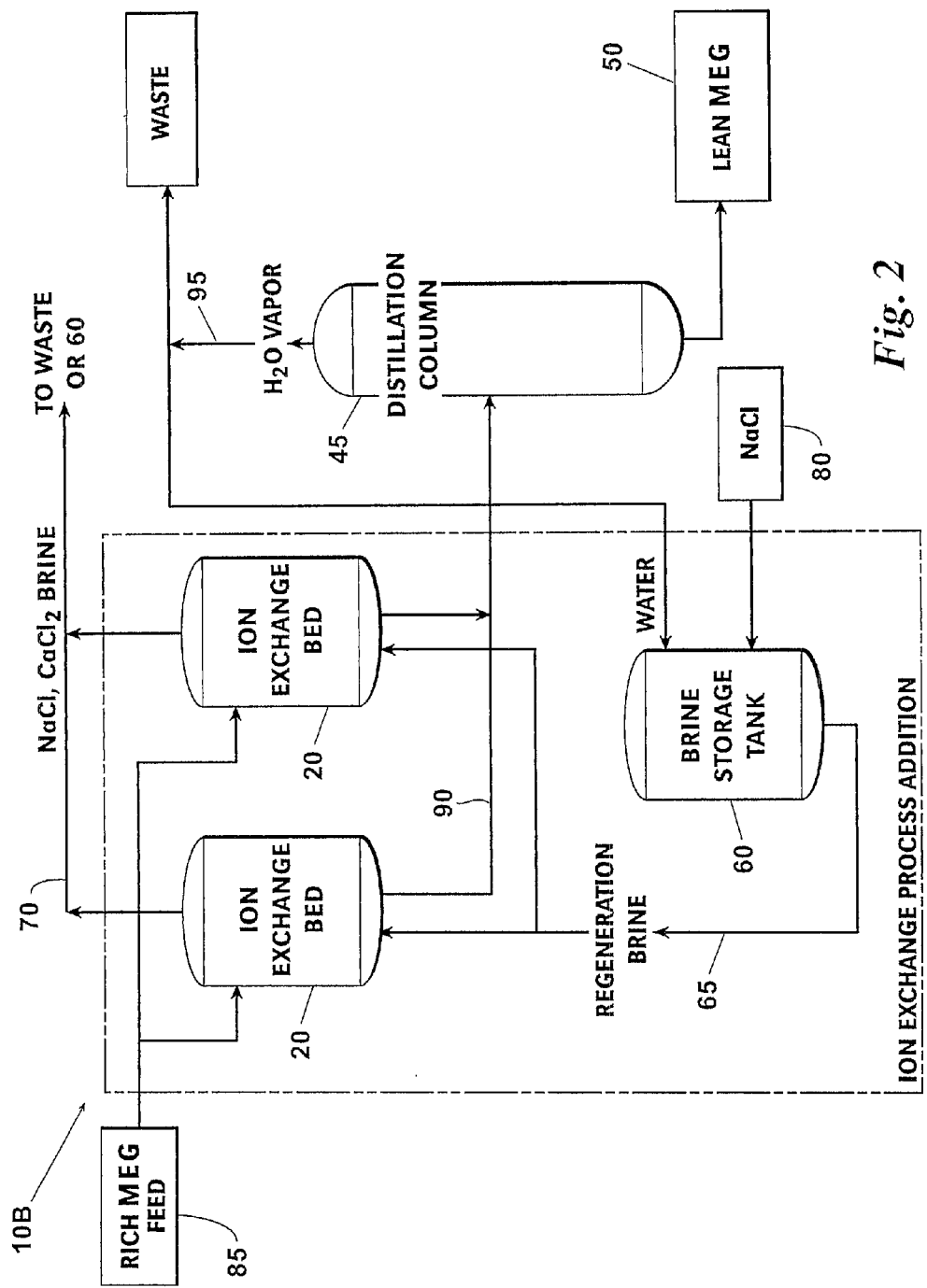
FIG. 2 presents an embodiment of a process for removing divalent cations from a rich MEG feed stream as part of a MEG regeneration process, practiced according to this invention.

An ion exchange process may be used to remove divalent cations from the rich MEG feed stream before the feed stream enters the MEG reclamation process, as shown in FIG. 1, or the MEG regeneration process, as shown in FIG. 2. This ion exchange process is different than conventional water treatment because the rich MEG feed stream is more viscous than water and interacts differently with the ion exchange resins. In addition, the ion exchange resins of the present invention are subject to higher concentrations of sodium and calcium than would generally be found in water treatment systems.

As shown in FIG. 1, a preferred embodiment of a divalent cation removal process 10A practiced according to this invention begins with the rich MEG feed stream 15, which is a mixture of produced water and MEG. The rich MEG feed stream 15 is routed to a divalent cation removal step comprised of dual ion exchange beds 20 which contain a strong cation exchange resin in the sodium form and alternate between adsorption and regeneration phases. In the adsorption phase, the resin removes divalent cations from the rich MEG feed stream 15 by adsorbing the divalent cations from the produced water and displacing the sodium cations. Although two ion exchange beds 20 are shown in FIG. 1, the ion exchange process may use more than two beds or a single bed.

The rich MEG stream with the majority of divalent cations removed 25 then exits the ion exchange beds 20 and flows to the MEG reclamation process. The MEG reclamation process begins in a flash separator 30, where the pressure is reduced in order to separate salts from the rich MEG and water. A sodium chloride waste stream 35 exits the bottom end of the flash separator 30, while the vaporized water and MEG stream 40 exits the top end and flows to the distillation column 45. The distillation column 45 uses partial condensation to separate the water and MEG components of the vaporized water and MEG stream 40. Lean MEG 50 exits the bottom end of the distillation column 45 and distilled water 55 is discharged from the top end of the distillation column 45. After meeting necessary quality requirements, the distilled water 55 may be discharged as waste or recycled to the brine storage tank 60.

Regeneration of the ion exchange beds 20 may be accomplished with water containing large amounts of a salt. In the embodiment described in FIG. 1, the sodium chloride waste stream 35 from the flash separator 30 is combined with distilled water 55 from the distillation column 45 in the brine storage tank 60 to form regeneration brine 65. At the beginning of the regeneration process, one of the ion exchange beds 20 is taken off-line by diverting the flow of the rich MEG feed stream 15 from that bed 20 to the alternate bed 20. A stream of regeneration brine 65 from the brine storage tank 60 is then routed through the off-line ion exchange bed 20 in a direction opposite that of the flow of the rich MEG feed stream 15. Divalent cations that have been adsorbed to the cation exchange resins inside the ion exchange bed 20 leave the resins and enter the stream of regeneration brine 65, forming a waste stream of sodium chloride and calcium chloride brine 70 that exits from the top of the ion exchange bed 20. The waste stream of sodium chloride and calcium chloride brine 70 can be disposed of as waste or re-used to regenerate the ion exchange beds 20.

As shown in FIG. 2, an ion exchange process may also be used to regenerate MEG by removing divalent cations from the rich MEG feed stream. This process may be used in applications where the produced water is relatively free of salts and the purity standards for MEG are less stringent. However, the MEG may contain divalent cations at a concentration that would cause equipment and scaling issues. Removing these ions protects downstream equipment and extends the useful life of the MEG.

A preferred embodiment of a divalent cation removal process 10B practiced according to this invention begins with a rich MEG feed stream 85, which is routed to a divalent cation removal step. The divalent cation removal step is comprised of dual ion exchange beds 20 which contain a strong cation exchange resin in the sodium form and alternate between adsorption and regeneration phases. In the adsorption phase, the resin removes divalent cations from the feed stream 85 by adsorbing the divalent cations from the produced water and displacing the sodium cations. Although two ion exchange beds 20 are shown in FIG. 2, the ion exchange process may use more than two beds or a single bed.

The rich MEG stream with the majority of divalent cations removed 90 then exits the ion exchange beds 20 and flows to a distillation column 45, which separates the water from the lean MEG. Lean MEG 50 exits the bottom end of the distillation column 45, while the vaporized water 95 exits the top end. After the vaporized water 95 cools, it may be discharged as waste or recycled to the brine storage tank 60.

Regeneration of the ion exchange beds 20 may be accomplished with water containing large amounts of a salt. In the embodiment described in FIG. 2, sodium chloride 80 from an external source is combined with the water 95 from the distillation column 45 in the brine storage tank 60 to form regeneration brine 65. At the beginning of the regeneration process, one of the ion exchange beds 20 is taken off-line by diverting the flow of the rich MEG feed stream 85 from that bed 20 to the alternate bed 20. A stream of regeneration brine 65 from the brine storage tank 60 is then routed through the off-line ion exchange bed 20 in a direction opposite that of the flow of the feed stream 85. Divalent cations that have been adsorbed to the ion exchange resins inside the ion exchange bed 20 leave the resins and enter the stream of regeneration brine 65, forming a waste stream of sodium chloride and calcium chloride brine 70 that exits from the top of the ion exchange bed 20. The waste stream of sodium chloride and calcium chloride brine 70 can be disposed of as waste or re-used to regenerate the ion exchange beds 20.

The present invention allows the MEG to remain in service for a longer period of time before the concentration of divalent cations increases to a level that could cause scaling or corrosion of the equipment. Another advantage of the present invention is that distilled water, which is produced during MEG reclamation and MEG regeneration and conventionally managed as a waste material, is recycled to form regeneration brine. Sodium chloride produced during MEG reclamation can also be recycled to form regeneration brine. Another advantage is that the waste stream of sodium chloride and calcium chloride brine from regeneration of the ion exchange beds contains only the salts that were originally present in the produced water. As a result, this waste stream can be discharged, if the appropriate water quality standards are met, to the marine environment or an injection well. This waste stream may also be recycled through the regeneration process for the cation exchange resin in the ion exchange beds until the concentration of divalent cations increases to a level that impairs regeneration of the resin.

While preferred embodiments of a system and process for removing divalent cations from a rich MEG feed stream have been described in detail, a person of ordinary skill in the art understands that certain changes can be made in the arrangement of process steps and type of components used in the system and process without departing from the scope of the following claims.

What is claimed is:

1. A process for removing divalent cations from a rich MEG feed stream, the process comprising the steps of:

passing the rich MEG feed stream through an ion exchange bed containing a cation exchange resin where the divalent cations are adsorbed by the cation exchange resin;

passing the rich MEG feed stream from the ion exchange bed through a flash separator which separates the feed stream into sodium chloride and water/MEG vapor; and passing the water/MEG vapor from the flash separator through a distillation column which separates the water/MEG vapor into distilled water and lean MEG.

2. A process according to claim 1 further comprising the step of regenerating the cation exchange resin by passing a regeneration brine through the ion exchange bed in a direction opposite that of the rich MEG feed stream.

3. A process according to claim 2 wherein the regeneration brine is held in a brine storage tank before it flows through the ion exchange bed.

4. A process according to claim 1 wherein the regeneration brine is comprised of sodium chloride produced as the rich MEG feed stream is treated in the flash separator.

5. A process according to claim 1 wherein the regeneration brine is comprised of water produced as the rich MEG feed stream is treated in the distillation column.

6. A process according to claim 3 further comprising the step of routing the regeneration brine to the brine storage tank after it has flowed through the ion exchange bed and re-using it to regenerate the cation exchange resin.

* * * * *